(12) United States Patent
Friedman

(10) Patent No.: US 7,094,057 B2
(45) Date of Patent: Aug. 22, 2006

(54) DENTAL LIGHT CURING MEMBER AND METHOD

(76) Inventor: Joshua Friedman, P.O. Box 2867, Danbury, CT (US) 06813

( * ) Notice: Subject to any disclaimer, the term of this patent is extended or adjusted under 35 U.S.C. 154(b) by 219 days.

(21) Appl. No.: 10/243,244

(22) Filed: Sep. 13, 2002

(65) Prior Publication Data

US 2004/0053189 A1   Mar. 18, 2004

(51) Int. Cl.
*A61C 3/00* (2006.01)
(52) U.S. Cl. .................. 433/140; 433/29; 433/226
(58) Field of Classification Search .............. 433/29, 433/37, 140, 216, 226, 71; 606/234, 235, 606/236; 607/88, 89, 92, 93; 385/129, 130, 385/132
See application file for complete search history.

(56) References Cited

U.S. PATENT DOCUMENTS

| | | | | |
|---|---|---|---|---|
| 3,753,266 A | * | 8/1973 | Ceniceros | 15/110 |
| 4,449,928 A | * | 5/1984 | von Weissenfluh | 433/40 |
| 4,553,936 A | * | 11/1985 | Wang | 433/37 |
| 4,571,188 A | | 2/1986 | Hamilton | |
| 4,716,902 A | * | 1/1988 | Swartz | 606/234 |
| 4,790,752 A | * | 12/1988 | Cheslak | 433/37 |
| 4,852,549 A | * | 8/1989 | Mori | 607/92 |
| 5,104,591 A | | 4/1992 | Masuhara | |
| 5,433,413 A | * | 7/1995 | Adams | 248/205.3 |
| 5,718,577 A | * | 2/1998 | Oxman et al. | 433/37 |
| 5,759,032 A | | 6/1998 | Bartel | |
| 5,813,854 A | * | 9/1998 | Nikodem | 433/29 |
| 6,015,403 A | * | 1/2000 | Jones | 606/4 |
| 6,743,249 B1 | * | 6/2004 | Alden | 607/88 |
| 2004/0038183 A1 | * | 2/2004 | Jacobs et al. | 433/215 |
| 2004/0043349 A1 | * | 3/2004 | Liao | 433/29 |

* cited by examiner

Primary Examiner—Todd E. Manahan

(57) ABSTRACT

The elastomeric member of the present invention is a flexible light guide and curing aid, which permits pressure to be applied to a photo curable material during the clinical restoration of a tooth while simultaneously curing the material by exposing the photo curable material to light. The method of the present invention permits the high forces developed between the occlusal surfaces of opposing teeth when engaged to be utilized to create the applied pressure on the photo curable material. The elastomeric member is soft and has an optically transparent body with a first section having first and second opposing planar surfaces adapted for placement in lateral juxtaposition between the occlusal surfaces of opposing teeth of human dentition and a second section extending from the first section adapted to facilitate contact with a dental light guide while the opposing teeth are engaged.

15 Claims, 4 Drawing Sheets

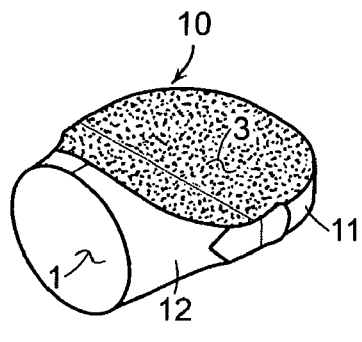
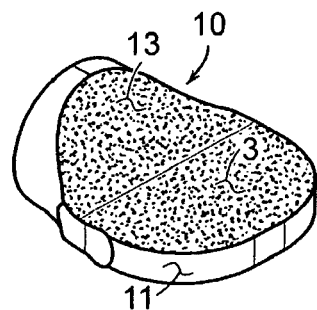
FIG. 1A          FIG. 1B
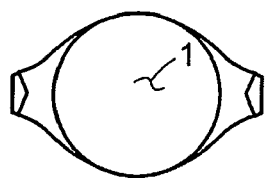
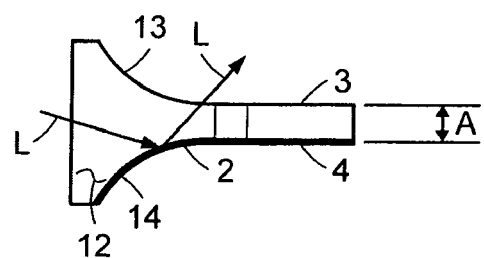
FIG. 1C          FIG. 1D

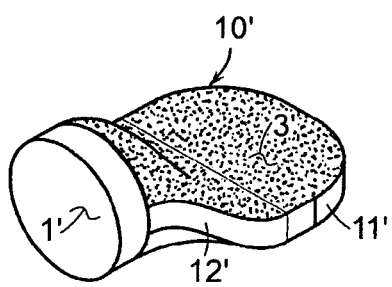
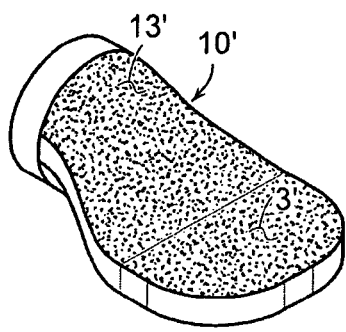
FIG. 3A FIG. 3C
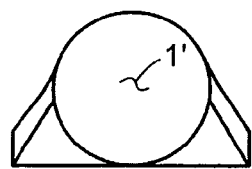
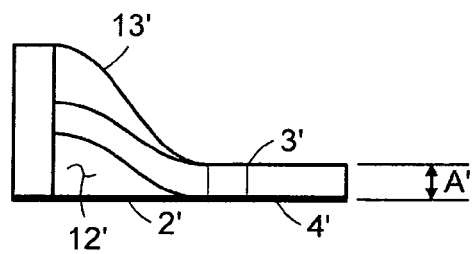
FIG. 3B FIG. 3D

DENTAL LIGHT CURING MEMBER AND METHOD

FIELD OF INVENTION

This invention relates to a dental device and method for use in conjunction with a light guide to enhance the polymerization of light activated restorative materials upon exposure to light during the clinical restoration of a tooth.

BACKGROUND OF THE INVENTION

Light curing restorative materials has been used in dentistry for over 20 years. Typically the dentist prepares a tooth as he would for a silver amalgam restoration but substitutes a light curable restorative material, which is cured by exposure to light generated from a curing unit light at a wavelength in the 400–500 nm range. In the past, various attempts have been made to adjust for the proper occlusal contour of the restoration as well as the bonding of the restoration to the tooth itself, both to the dentin and to the enamel. Despite efforts of the dentist, micro leakage remains a major problem and occurs when either the filling material is not well adapted to the cavity walls or the restoration shrinks in the curing process to something less than the size of the prepared cavity into which the material is placed. At the microscopic level this results in an open margin between the restorative material and the tooth structure and in turn provides a site for bacterial invasion and subsequent breakdown of the restorative material as well as caries or tooth decay in the tooth structure itself.

In the industrial field, by comparison, when plastic or plastic like materials are molded, they are always molded under pressure and in so doing the material is caused to adapt very closely to the mold cavity. The concept of applying pressure to a photo curable material simultaneously with the application of light to improve adaptation during polymerization is taught in U.S. Pat. No. 4,571,188 (Hamilton). This patent teaches fabricating a transparent occlusal matrix, which is placed over the light curable composite before pressure is applied to the matrix. The composite is then cured by passing light through the transparent matrix. However, it is necessary to specifically fabricate a custom transparent occlusal matrix to match the occlusal surfaces of each restoration, which is time consuming, cumbersome and inconvenient. Moreover, it is difficult to cause adequate external pressure to be applied to the occlusal surface through the transparent matrix and to have a significant effect on the compression of the restorative material.

Another method for applying pressure to a photo curable material simultaneously with the application of light is taught in U.S. Pat. No. 5,759,032 (Bartel) through use of an accessory adapted to fit over the light-emitting tip of a light guide. This approach however does not address the problem of occlusal contact with the opposing dental arch which will differ for every patient so that once the restoration is polymerized the teeth can come into normal occlusal contact. In addition, the pressure applied to the restoration is limited by the fragility of the conventional glass light guides in common use today. Furthermore, it is awkward and difficult to generate sufficient pressure through the handle of a dental light gun or wand to create a significant effect on the compression of the dental restorative material.

Yet another method for curing photo curable composites under light while applying pressure is taught in U.S. Pat. No. 5,104,591 (Massuhara et al) but is limited to an application in a dental laboratory when creating a mold from an impression and is designed only for use outside the mouth. This method is not adaptable for use by a dentist to the clinical restoration of a tooth within a patient's mouth.

SUMMARY OF THE INVENTION

The dental device of the present invention is a light curing aid, which permits pressure to be applied to a photo curable composite during the clinical restoration of a tooth while simultaneously curing the composite by exposing the photo curable composite to light generated from a conventional curing light. The present invention utilizes the forces developed between the occlusal surfaces of opposing teeth when the opposing teeth are engaged to create the applied pressure on the photo curable composite permitting light to be simultaneously applied from a light guide to cure the material while under pressure.

The dental device of the present invention is a soft elastomeric member having an optically transparent body comprising a first section having first and second opposing planar surfaces adapted for placement in lateral juxtaposition between the occlusal surface of the tooth to be restored and the occlusal tooth surface of the opposing dental arch with one of said opposing planar surfaces. One surface is adapted to contact the photo curable restorative material located in the tooth to be restored and a second section extending from the first section with the second section having a proximal surface adapted to facilitate contact with a light guide from a dental curing light while the opposing teeth are engaged. The elastomeric member should be optically transparent and wherein the planar surface in contact with the photo curable composition should preferably have a textured non-smooth surface and the planar surface in contact with the occlusal surface of the opposing arch should preferably be a reflective smooth surface.

The method of the present invention comprises the steps of: forming a soft elastomeric member having an optically transparent body, a first section with first and second opposing planar surfaces and a second section extending from the first section; placing the first section in lateral juxtaposition between the occlusal surface of the tooth to be restored and the occlusal tooth surface of the tooth in the opposing dental arch with the first planar surface in contact with the light activated restorative material and the second planar surface in contact with the occlusal surface of the tooth in the opposing arch; instructing the dental patient to bite down on the first section; placing a light guide from a curing light against the second section; generating light from the curing light at a wavelength of between 400 to 500 nm to initially polymerize the light activated restorative material and removing the soft elastomeric member from the patient and completing the direct polymerization so as to fully cure the light activated restorative material.

BRIEF DESCRIPTION OF THE DRAWINGS

Other objects and advantages of the present invention will become apparent from the following detailed description of the present invention when read in conjunction with the accompanying drawings of which:

FIGS. 1(a–d) show the light curing dental device of the present invention with FIGS. 1(a) and 1(b) showing the device of the present invention in perspective but oriented at a different angle relative to one another, FIG. 1(c) showing a front view of the device and FIG. 1(d) showing the device of the present invention in side elevation;

FIGS. 3(a–d) show an alternate embodiment of the present invention similar to the embodiment of FIGS. 1(a–d) with FIGS. 3(a) and 3(c) showing the device of FIG. 3 in perspective but oriented at a different angle relative to one another, FIG. 3(b) showing a front view of the device of FIG. 3 and FIG. 3(d) showing the device of FIG. 3 in side elevation.

DETAILED DESCRIPTION OF A PREFERRED EMBODIMENT

The dental device of the present invention is an elastomeric member 10 having a transparent body as shown in FIGS. 1(a), 1(b), 1(c) and 1(d) and FIGS. 2(a) and 2(b) as well as in FIGS. 3 and 4 identified as 10' and 10" respectively. The elastomeric member 10 is transparent and intended for use as a flexible light guide to facilitate curing a photo curable resin composition during the clinical restoration of a tooth while simultaneously directing light into the elastomeric member 10 to polymerize the photo curable composition under pressure. The dental device may be formed of any elastomeric material including, for example, a silicone composition, a urethane composition or an elastomeric acrylic selected from a broad range of acrylics known as thermoplastic elastomers. The elastomeric member 10 should be soft having a preferred durometer of between Shore 00 #20 and 00 #60 and optimally having a durometer of Shore 00 #35 and 00 #45.

Figure 2A:
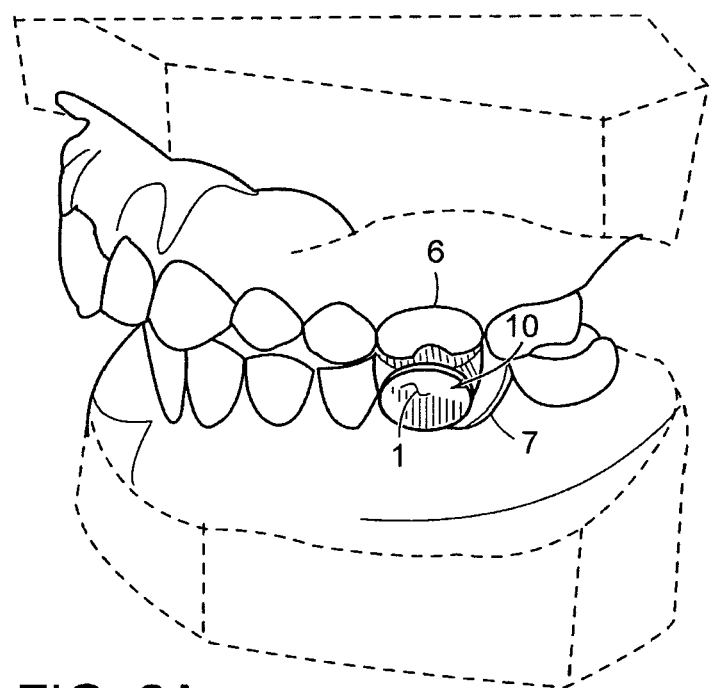
FIGS. 2(a) and 2(b) are perspective views of a dental model showing the two arches of opposing teeth of the human anatomy with the light curing dental device of the present invention shown in both figures positioned between two occlusal biting surfaces of the opposing teeth and in FIG. 2(b) also showing a light guide in proximity to the front face of the light curing dental device for curing a photo curable composite in one of the opposing teeth.

The elastomeric member 10 can be of any geometry comprising at least one section 11 of a predetermined thickness "A" having two opposite planar surfaces 2 and 3 which are adapted for placement between two occlusal biting surfaces of two opposing teeth of the human dentition as is illustrated in the model of dental teeth shown in FIG. 2(a) with one of the two opposing teeth having been prepared to be restored by inclusion of a photo curable restorative material and further comprising a second section 12 extending from the first section 11. The second section 12 has a proximal surface 1 adapted for contact with a light guide. The proximal surface 1 may be flat or concave in geometry and should lie in a plane disposed substantially transverse, but no more than 45 from perpendicular to the opposite planar surfaces 2 and 3 of the first section 11 when the member 10 is in the non-compressed state. When the member 10 is placed between two occlusal biting surfaces of opposing teeth the proximal surface 1 of the second section 12 lies substantially parallel to the buccal surfaces of the opposing teeth. The word substantial is intended to permit a deviation of up to thirty-three degrees.

Figure 2B:
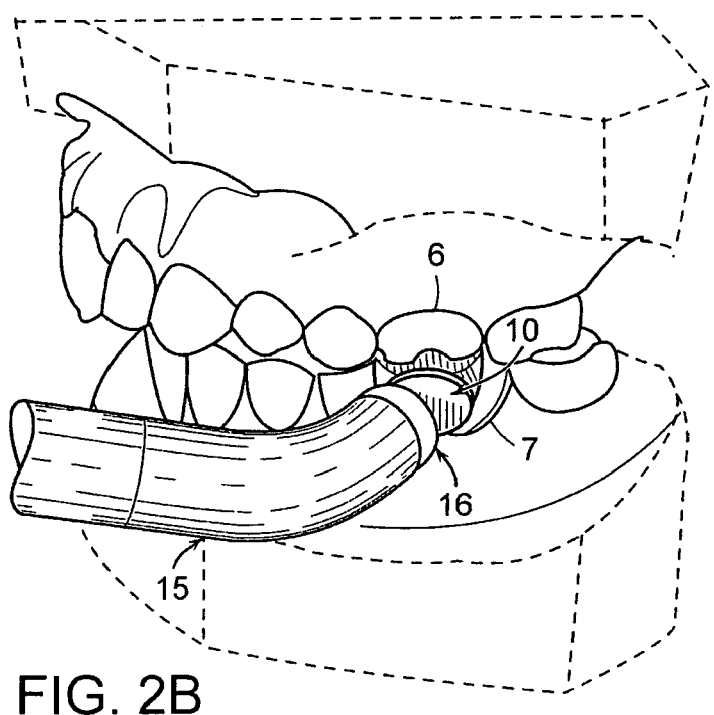
Figure 4A:
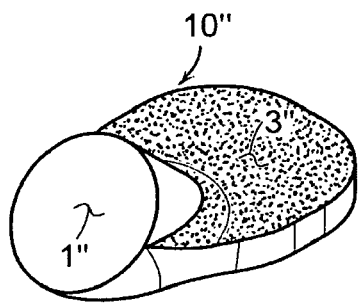
FIGS. 4(a–d) showing yet another alternate embodiment of the present invention similar to the embodiment of FIGS. 1(a–d) and FIGS. 3(a–d) in which FIGS. 4(a) and 4(c) showing the device of FIG. 4 in perspective but oriented at a different angle relative to one another, FIG. 4(b) showing a front view of the device of FIG. 4 and FIG. 4(d) showing the device of FIG. 4 in side elevation.
Figure 4C:
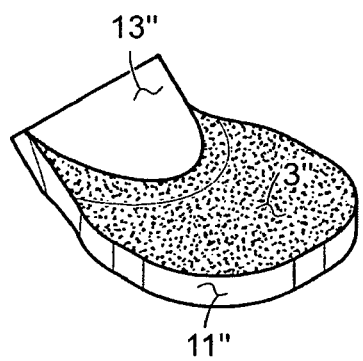
Figure 4B:
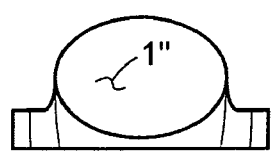
Figure 4D:
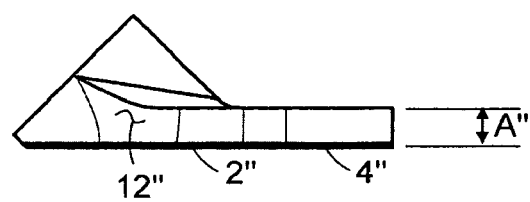

Either one of the two opposing teeth 6 and 7 as shown in FIG. 2(a) or 2(b), between which the member 10 is placed, may represent the tooth to be restored and will initially have been prepared by a dentist for restoration by placing a conventional light curable restorative composition into a prepared cavity (not shown) within the tooth. The first section 11 is inserted with the planar surface 3 placed over and adjacent to the light curable restorative composition in the tooth to be restored so that the opposing planar surface 2 with a reflective coating 4 will make contact with the occlusal surface of an opposing tooth from the opposite arch when engaged as is shown in FIGS. 2(a) and 2(b). The reflective coating should cover both surfaces 4 and 11 to provide maximum internal reflection and thus improve the optical transmission efficiency of this device. If the restoration were in the tooth in the lower arch the member 10 would still be inserted so that the planar surface 3 of the first planar section 11 would contact the light curable restorative composition in the tooth of the lower arch and the opposing planar surface 2 would contact the occlusal surface of the opposing tooth in the upper arch when the teeth are engaged.

All of the surfaces of the elastomeric member 10 should be smooth and polished to provide optically clear surfaces except for the surface 3, which represents the light output surface of the member 10. The surface 3 is preferably sandblasted to form a textured surface finish, which is not smooth. This is to cause light to emerge from this surface 3 into the photo curable composition without being internally refracted. The optical characteristics of the member 10 should be such that the member 10 is optically clear in the 400–500 nm range with all surfaces polished except the light output surface 3.

The opposite planar surface 2 of member 10 should be reflective. To improve the reflective property of the planar surface 2 it may be coated with a layer 4 having a reflective white or silver finish. Alternatively, all of the surfaces of the member 10 may be coated with a reflective white or silver finish except for the front proximal surface 1 and the light output surface 3 facing the photo curable composition.

Section 12 is preferably integrally formed with that of section 11 from a single mold and may have curved portions 13 and 14 extending from the opposite planar side surfaces 2 and 3 to the proximal surface 1 of section 12. The curved portions 13 and 14 provide structural integrity to assure proper alignment of section 12 relative to the anterior mesial surfaces of the teeth 6 and 7 when the member 10 is compressed as shown in FIGS. 2(a) and 2(b) respectively. The curved portion 13 extending from the output surface 3 should have a sandblasted or textured non smooth surface finish which is similar to surface 3 and the curved portion 14 should have a smooth surface similar to surface 2. The proximal face 1 of section 12 should be smooth and polished and should preferably be circular or oval in shape having a diameter in a range generally between 7–13 mm and preferably between about 8–11 mm in diameter.

The thickness "A" of section 11 is relatively important and represents the occlusal thickness of the member 10 into which the opposing teeth bite. If this dimension is too thick the occlusal adjustment may become overcompensated and the tooth to be restored may be out of occlusion when exposed to light. If section 11 is too thin then not enough radiant light energy will be transferred to the surface of the restoration to provide for satisfactory polymerization of the photo curable composition. Accordingly the thickness of section 11 corresponding to dimension "A" should lie in a range of about 1 to 3 mm when the member 10 is in the non-compressed state and more preferably between 0.25–1.5 mm thick in the compressed state. When member 10 is compressed section 11 should conform in anatomical shape to the opposite occlusal surfaces of the opposing arch.

In clinical operation, after a dentist places the photo curable restorative material in the prepared cavity of the tooth to be restored the device 10 is placed between the opposing teeth such that the planar surface 3 of section 11 lies upon an occlusal surface in contact with the restorative composite material of the tooth to be restored and the planar surface 2 (and 4) makes contact with the occlusal surface of the tooth in the opposing arch. The patient is then instructed to bite down on the elastomeric member 10 as shown in FIGS. 2(*a*) and 2(*b*) respectively. Since the elastomeric member 10 is quite soft it will readily conform to the anatomy of the occusal surfaces of the opposing teeth to cause the biting pressure applied to the member 10 to be transferred uniformly to the restorative material. When teeth are in occlusion, biting pressures of up to 22,000 psi are not unusual. Simultaneously, light from a conventional light curing gun is directed through a light guide 15 as shown in FIG. 2(*b*), with the tip 16 of the light guide 15 placed adjacent the proximal surface 1 of the member 10 causing light as depicted by the arrows L in FIG. 1(*d*) to travel from the proximal surface 1 through the transparent body of the member 10 and to reflect off the surface 2 with the light emerging from the surface 3 into the photo curable composition for curing the material.

FIGS. 3 and 4 are alternate embodiments of the device of FIG. 1 with each constructed to provide a slightly different geometrical shape. The curved surface 14 as shown in FIG. 1(*d*) has been eliminated from the embodiment of FIGS. 3 and 4 so that the device 10' and 10" form a flat bottom with the planar surfaces 4' and 4" extending to the proximal faces 1' and 1" of section 12' and 12" respectively. The design of FIG. 3 and FIG. 4 offer similar performance with that of FIG. 1, but with the additional advantage that a white or silver coating 4' and 4" is easier to apply in the manufacturing of the device because the reflecting surfaces 2' and 2" are continuous flat horizontal surfaces extending from the proximal surfaces of section 12' and 12" respectively.

FIG. 4 is a modification of FIG. 3 in which section 12" is angled so that the proximal surface 1" lies at an acute angle from above zero degrees to 60 degrees to the horizontal reflecting surface 2" and preferably at an angle of between 30 to 45 degrees. The design of FIG. 4 is particularly useful when the buccal space in a patient's mouth is limited. This permits mounting or placing a curing light guide 15 and 16 on the surface 1" more easily without having to greatly extend the patient's cheek.

In accordance with the present invention it is not necessary to fully polymerize the photo curable composition throughout the entire restoration. Instead it is only necessary to cause the photo curable composition to be polymerized at all of its outer surfaces and margins to seal the margins. Once the margins are sealed, micro leakage is prevented. It is the outer surfaces of the photo curable composition, which need to be sealed to eliminate micro leakage and in so doing cause better adaptation between the tooth and the restorative material. The restoration is compressed and adapts more closely to the cavity walls of the tooth to be restored providing much better retention and bond strength. The photo curable composition can then be more fully cured occlusally and/or buccal-lingually in a second step following initial polymerization. The second step need not be conducted under pressure or using the member 10 but may instead be performed after removal of the member 10 from the mouth of the patient so as to achieve complete polymerization in two steps. Little if any occlusal adjustment is further required because of the dynamic and anatomical nature in which this restoration was formed.

A problem with light cured restorative materials currently on the market is that they exhibit a surface oxygen inhibited layer. This appears as a waxy film that is typically polished off by the dentist. Another important feature of our invention is that because of the absence of surface oxygen in the curing process due to the tight adaptation of the elastomeric material against the restorative material a glass like smooth finish results with few porosity and little if any adjustments or polishing if further needed.

What is claimed is:

1. A dental bite member composed of a soft elastomeric material composition adapted to be placed in contact between two opposing occlusal biting surfaces of human dentition during the preparation of a dental restoration in situ, with at least one of the opposing teeth containing a photo curable restorative material, wherein pressure is applied against said restorative material by biting down upon the dental bite member while transmitting light from a light guide into said dental bite member to cure the restorative material, said bite member comprising; a first section with two opposing planar surfaces for engaging at least two of said occlusal biting surfaces in the opposing teeth and a second section extending from the first section wherein the first section lies in a plane substantially parallel to the occlusal biting surfaces and the second section has a planar optically smooth surface aligned at an angle relative to the plane of said first section and the first and second section are in an arrangement relative to one another such that when the light guide is placed against said second section light is caused to enter said dental bite member through said optically smooth surface in a direction substantially perpendicular thereto and is caused to exit said first section in a substantially transverse direction to cure said photo curable restorative material while pressure is being applied.

2. A dental bite member as defined in claim 1 wherein said member has an optically transparent body.

3. A dental bite member as defined in claim 2 wherein said elastomer member has a durometer between shore 00 #20 and 00 #60.

4. A dental bite member as defined in claim 3 wherein said elastomer member has a durometer between shore 00 #35 and 00 #45.

5. A dental bite member as defined in claim 3 wherein said second section has a proximal surface adapted for contacting the distal end of said light guide.

6. A dental bite member as defined in claim 3 wherein said proximal surface lies in a plane substantially transverse to said first section.

7. A dental bite member as defined in claim 6 wherein the thickness of said first section lies in a range of about 1 to 3 mm when the member is in a non-compressed state.

8. A dental bite member as defined in claim 5 wherein said second section lies at an angle relative to said first section of from between above zero degrees to 60 degrees.

9. A dental bite member as defined in claim 5 wherein the planar surface in contact with the light activated restorative material has a textured non-smooth surface and wherein the planar surface in contact with the occlusal surface of a tooth in the opposing arch has a smooth surface which is reflective.

10. A dental bite member as defined in claim 9 wherein the reflective planar surface in contact with the occlusal surface of a tooth in the opposing arch forms a flat horizontal surface extending from said second section.

11. A dental bite member as defined in claim 9 wherein said flat horizontal surface has a coating of a reflective white or silver finish.

12. A dental bite member as defined in claim 9 wherein the reflective planar surface in contact with the occlusal surface of a tooth in the opposing arch is a flat horizontal surface having a coating of a reflective white or silver finish.

13. A dental bite member as defined in claim 12 wherein the thickness of said first section lies in a range of about 0.25 to 1.5 mm when the member is in a compressed state.

14. A dental bite member as defined in claim 5 wherein the planar surface in contact with the light activated restorative material has a textured non-smooth surface and wherein the planar surface in contact with the occlusal surface of a tooth in the opposing arch has a smooth surface.

15. A method for curing a dental restoration in a tooth of a dental patient filled with light activated restorative material (s) comprising the steps of: forming a dental bite member having an optically transparent body of a soft elastomeric material composition, a first section with first and second opposing planar surfaces and a second section extending from the first section; placing the first section in lateral juxtaposition between the occlusal surface of the tooth to be restored and the occlusal tooth surface of the tooth in the opposing dental arch with the first planar surface in contact with the light activated restorative material and the second planar surface in contact with the occlusal surface of the tooth in the opposing arch; instructing the dental patient to bite down on the first section; placing a light guide from a curing light against the second section; generating light from the light gun at a wavelength of between 400 to 500 nm to initially polymerize the light activated restorative material and removing the soft elastomeric member from the patient and completing the polymerization so as to fully cure the light activated restorative material.

* * * * *